US012662502B2

(12) United States Patent
Kawamoto et al.

(10) Patent No.: US 12,662,502 B2
(45) Date of Patent: Jun. 23, 2026

(54) METHOD FOR PRODUCING SUGAR ANHYDRIDE AND SACCHARIDE

(71) Applicants: KYOTO UNIVERSITY, Kyoto (JP); SHIN-ETSU CHEMICAL CO., LTD., Tokyo (JP)

(72) Inventors: Haruo Kawamoto, Kyoto (JP); Eiji Minami, Kyoto (JP); Takashi Nomura, Kyoto (JP); Hinano Mizuno, Kyoto (JP); Kazuto Kobayashi, Tokyo (JP); Akiko Miki, Tokyo (JP)

(73) Assignees: KYOTO UNIVERSITY, Kyoto (JP); SHIN-ETSU CHEMICAL CO., LTD., Tokyo (JP)

( * ) Notice: Subject to any disclaimer, the term of this patent is extended or adjusted under 35 U.S.C. 154(b) by 876 days.

(21) Appl. No.: 17/797,489

(22) PCT Filed: Feb. 26, 2021

(86) PCT No.: PCT/JP2021/007228

§ 371 (c)(1),
(2) Date: Aug. 4, 2022

(87) PCT Pub. No.: WO2021/172482

PCT Pub. Date: Sep. 2, 2021

(65) Prior Publication Data

US 2023/0067889 A1    Mar. 2, 2023

(30) Foreign Application Priority Data

Feb. 27, 2020   (JP) ................................. 2020-032050

(51) Int. Cl.
*C07H 3/10* (2006.01)
*C07H 1/00* (2006.01)
*C13K 1/02* (2006.01)

(52) U.S. Cl.
CPC ................. *C07H 3/10* (2013.01); *C07H 1/00* (2013.01); *C13K 1/02* (2013.01)

(58) Field of Classification Search
CPC ............... C07H 3/10; C07H 1/00; C13K 1/02
USPC .......................................................... 127/37
See application file for complete search history.

(56) References Cited

FOREIGN PATENT DOCUMENTS

| JP | 58-152001 A | 9/1983 | | |
| JP | 2006-28040 A | 2/2006 | | |
| JP | 2007-21471 A | 2/2007 | | |
| WO | WO-2007092898 A2 * | 8/2007 | ............... | C13K 1/02 |

OTHER PUBLICATIONS

Selective saccharification of microwave-assisted glycerol pretreated corncobs via fast pyrolysis and enzymatic hydrolysis Fuel, vol. 265, p. 3, Apr. 1, 2020, (Year: 2020).*

Boiling point of levoglucosan and devolatilization temperatures in cellulose pyrolysis measured at different heating area temperatures Journal of Analytical and Applied Pyrolysis vol. 109, Sep. 2014, pp. 185-195 (Year: 2014).*

Abdilla-Santes et al., "Conversion of levoglucosan to glucose using an acidic heterogeneous Amberlyst 16 catalyst: Kinetics and packed bed measurements", Chemical Engineering Research and Design, 2019, vol. 152, pp. 193-200.

Fukutome et al., "Processes forming Gas, Tar, and Coke in Cellulose Gasification from Gas-Phase Reactions of Levoglucosan as Intermediate", ChemSusChem, 2015, vol. 8, pp. 2240-2249.

Gunawan et al., "Hydrolysis and glycosidation of sugars during the esterification of fast pyrolysis bio-oil", Fuel, 2012, vol. 95, pp. 146-151.

International Search Report, issued in PCT/JP2021/007228, dated May 18, 2021.

Jiang et al., "Comprehensive utilization of glycerol from sugarcane bagasse pretreatment to fermentation", Bioresource Technology, 2015, vol. 196, pp. 194-199.

Jiang et al., "Crude glycerol pretreatment for selective saccharification of lignocellulose via fast pyrolysis and enzyme hydrolysis", Energy Conversion and Management, 2019, vol. 199, 111894, pp. 1-7.

Jiang et al., "Effect of Glycerol Pretreatment on Levoglucosan Production from Corncobs by Fast Pyrolysis", Polymers, 2017, vol. 9, No. 11, 599, pp. 1-12.

Jiang et al., "Selective saccharification of microwave-assisted glycerol pretreated corncobs via fast pyrolysis and enzymatic hydrolysis", Fuel, 2020, vol. 265, 116965, pp. 1-7.

Kwon et al., "Rapid-cooling, continuous-feed pyrolyzer for biomass processing Preparation of levoglucosan from cellulose and starch", J. Anal. Appl. Pyrolysis, 2007, vol. 80, pp. 1-5.

Shafizadeh et al., "Production of Levoglucosan and Glucose from Pyrolysis of Cellulosic Materials", Journal of Applied Polymer Science, 1979, vol. 23, pp. 3525-3539.

Shoji et al., "Boiling point of levoglucosan and devolatilization temperatures in cellulose pyrolysis measured at different heating area temperatures", Journal of Analytical and Applied Pyrolysis, 2014, vol. 109, pp. 185-195.

Written Opinion of the International Searching Authority, issued in PCT/JP2021/007228, dated May 18, 2021.

Yang et al., "Overcoming biomass recalcitrance to enhance platform chemical production from soft wood by organosolvolysis coupled with fast pyrolysis", Cellulose, 2019, vol. 26, pp. 9687-9708.

* cited by examiner

*Primary Examiner* — Coris Fung

(74) *Attorney, Agent, or Firm* — Birch, Stewart, Kolasch & Birch, LLP

(57) ABSTRACT

A method for producing sugar anhydride, comprising: (1) first heat treatment step of heating polysaccharide having reducing end group at 130-350° C. in the presence of C1-C10 alcohol compound free of an acetal structure; (2) second heat treatment step of heating the first heat treated polysaccharide for pyrolysis to form a gaseous sugar anhydride, the second heat treatment forming no char or only filmy char and forming no carbon monoxide or some carbon monoxide such that the amount of carbon monoxide formed is not more than 5 parts by weight per 100 parts by weight of the absolute dry weight of the polysaccharide; and (3) recovery step of cooling the gaseous sugar anhydride to a temperature not higher than the boiling point thereof. According to this method, sugar anhydride can be easily produced at a high yield.

9 Claims, No Drawings

METHOD FOR PRODUCING SUGAR ANHYDRIDE AND SACCHARIDE

TECHNICAL FIELD

This invention relates to methods for producing sugar anhydrides and saccharides.

BACKGROUND ART

Cellulose base biomass originating from such plants as wood and cotton is a biomass resource which is most plenty and readily accessible on the earth. Because of non-edibility, it has been used in the human history mainly as fuels, building materials, textiles for clothes or the like, paper, and base polymers for semi-chemical synthetic polymers. Recently, cellulose base biomass is utilized for conversion to chemical materials useful as regenerative resources replacing fossil resources such as oil and natural gas. This is expected to contribute to a reduction of the carbon dioxide buildup in the air which is regarded the cause of global warming. At the present stage, such conversion has not been fully elucidated and developed.

While cellulose is a class of naturally occurring polymers consisting of linearly polymerized β-glucose units, saccharides converted from cellulose and anhydrides thereof (or anhydro-saccharides) are useful chemical substances which can be utilized as raw materials for the synthesis of medicines. If these chemical substances are converted from non-edible cellulose base biomass in an economic and rational way, they can be a replacement for edible resources (e.g., cereals) which are essentially used as food, but secondarily used for obtaining such chemical substances. The conversion is of great significance from the standpoint of food supply to the currently increasing human being.

For the conversion of cellulose base biomass to saccharides as one of the conversion technologies, acid hydrolysis, super- or sub-critical water extraction, and pyrolysis methods are known in the art. The acid hydrolysis and super- or sub-critical water extraction methods must overcome many problems including disposal of waste acids, severe reaction conditions, and difficult concentration of saccharide aqueous solution before their practical application.

On the other hand, the pyrolysis method is a method including pyrolysis to form sugar anhydride and subsequent hydrolysis of sugar anhydride into saccharide, and has advantages including no need for acid, and easy concentration of saccharide solution when conducted under dry conditions. Owing to these advantages, the product can be utilized as fermentation raw material for which high concentration saccharide solution is favored.

The pyrolysis method, however, has some problems. From the pyrolysis reaction, various volatile products such as furfural derivatives and carbides are by-produced. The thus produced sugar anhydrides undergo secondary decomposition in gas phase through fragmentation that they are further decomposed into smaller molecules such as carbon monoxide, carbon dioxide, methane and ethylene, and in liquid phase through polymerization. This makes it difficult to obtain sugar anhydrides in high yields. Additionally, furfural by-products largely affect the subsequent fermentation process because they are fermentation inhibitors.

As a method for producing a sugar anhydride through pyrolysis of cellulose base biomass that deals with the outstanding problems, for example, Non-Patent Document 1 reports a method for producing levoglucosan (1,6-anhydro-β-D-glucopyranose) by heating a cellulose-containing material, from which inorganic matter has been removed by acid washing, under reduced pressure or nitrogen flow in a tubular furnace at a temperature of 300 to 500° C. Also, Patent Document 1 describes a method for producing anhydro sugar, typically levoglucosan by uniformly suspending hexosan or hexosan-containing raw material in a high-boiling organic solvent, heating the suspension under atmospheric pressure at a temperature of 190 to 300° C. to form a reaction mixture containing anhydro sugar, isolating or purifying anhydro sugar from the reaction mixture by column chromatography. Further, Patent Document 2 and Non-Patent Document 2 describe a method for producing levoglucosan by heating a solid or liquid organic matter in an inert atmosphere for causing evaporation or pyrolysis, for letting the matter gasify as a volatile low-molecular-weight compound and recovering the product through a recovery unit while preventing secondary pyrolysis thereof.

PRIOR ART DOCUMENTS

Patent Documents

Patent Document 1: JP-A 2006-028040
Patent Document 2: JP-A 2007-021471

Non-Patent Documents

Non-Patent Document 1: J. Appl. Polym. Sci. (1979), 23, pp. 3525-3539
Non-Patent Document 2: J. Anal. Appl. Pyrolysis (2007), 80, pp. 1-5
Non-Patent Document 3: J. Anal. Appl. Pyrolysis (2014), 109, pp. 185-195
Non-Patent Document 4: ChemSusChem, 8 (2015) pp. 2240-2249

SUMMARY OF INVENTION

Technical Problem

However, the yield prior to purification of levoglucosan from the raw material, cellulose remains in the ranges of up to 58% by weight in Non-Patent Document 1, 39 to 58% by weight in Patent Document 1, and 37.1 to 70.4% by weight in Patent Document 2. When it is considered that the yield after purification will be further reduced, a further improvement in yield is needed.

Further, the concentration of levoglucosan in a tar recovered as the product in Non-Patent Document 1 is 30 to 68% by weight, and the concentration of levoglucosan in a syrup recovered as the product in Patent Document 2 is 55.0 to 81.1% by weight when starting from cellulose. An improvement in the purity of levoglucosan in the recovered product is also needed. Particularly when the product is used as a fermentation raw material, the purifying step is essential for removing furfural derivatives which are fermentation inhibitors.

In addition, Patent Document 1 not only uses a high-boiling organic solvent, but also needs to finely divide a raw material into a fine powder in order to achieve uniform suspension of the raw material. Patent Document 2 needs to furnish a special unit under reduced pressure and to supply a powdery or granular raw material as a thin layer of 5 mm or less. A heat decomposition time of at least 30 minutes is required for the treatment of 5 g of the raw material. Thus, an improvement is needed from the standpoint of simplicity of the producing method as well.

An object of the invention, which has been made under the above-mentioned circumstances, is to provide a method for simply producing sugar anhydride in high yields and a method for producing a saccharide from the sugar anhydride.

Solution to Problem

Making extensive investigations to solve the outstanding problems, the inventors have found that by heating a polysaccharide having a reducing end-group in the presence of an acetal structure-free alcohol compound of 1 to 10 carbon atoms and subjecting the polysaccharide to pyrolysis, a sugar anhydride is simply obtained in high yields. The invention is predicated on this finding.

One embodiment of the invention is a method for producing a sugar anhydride, comprising the first heat treatment step of heating a polysaccharide having a reducing end-group at 130 to 350° C. in the presence of an alcohol compound of 1 to 10 carbon atoms free of an acetal structure, the second heat treatment step of heating the first heat treated polysaccharide for pyrolysis to form a gaseous sugar anhydride, the second heat treatment forming no char or only filmy char and forming no carbon monoxide or some carbon monoxide such that the amount of carbon monoxide formed is not more than 5 parts by weight per 100 parts by weight of the absolute dry weight of the polysaccharide, and the recovery step of cooling the gaseous sugar anhydride to a temperature not higher than the boiling point thereof and recovering the sugar anhydride.

Another embodiment of the invention is a method for producing a saccharide comprising the step of hydrolyzing the sugar anhydride obtained by the above method in the presence of a solid acid catalyst while heating.

Advantageous Effects of Invention

According to the invention, a sugar anhydride and saccharide are produced from polysaccharide in high yields and with a high purity. Also, the pyrolysis of polysaccharide can be completed under atmospheric pressure within a short time of up to 60 seconds, without a need for special apparatus. Further, the raw material, polysaccharide can be used in any form including sheet, powder, fiber or particle form. Since the raw material is pyrolyzed under dry conditions without using an organic solvent, it is easy to concentrate the saccharide solution.

DESCRIPTION OF EMBODIMENTS

<Method for Producing Sugar Anhydride>

The invention provides a method for producing a sugar anhydride, comprising (1) the first heating step of conducting first heat treatment of heating a polysaccharide having a reducing end-group at 130 to 350° C. in the presence of an alcohol compound of 1 to 10 carbon atoms free of an acetal structure, (2) the second heating step of conducting second heat treatment of heating the first heat treated polysaccharide for pyrolysis to form a gaseous sugar anhydride, the second heat treatment forming no char or only filmy char and forming no carbon monoxide or some carbon monoxide such that the amount of carbon monoxide formed is not more than 5 parts by weight per 100 parts by weight of the absolute dry weight of the polysaccharide, and (3) recovery step of cooling the gaseous sugar anhydride to a temperature not higher than the boiling point thereof and recovering the sugar anhydride.

[Step (1): First Heating Step]

The first heating step is to conduct first heat treatment of heating a polysaccharide having a reducing end-group at 130 to 350° C. in the presence of an alcohol compound of 1 to 10 carbon atoms free of an acetal structure.

The polysaccharide is not particularly limited as long as it has a reducing end-group. Examples include cellulose, cellulose-containing materials such as pulp, starch, amylose, amylopectin, hemicelluloses (e.g., xylan, glucomannan, and galactan), chitin, and chitosan. Of these, cellulose and cellulose-containing materials are preferred from the aspect of a wide range of utilization as paper, film and clothing, with cellulose being most preferred.

The form of the polysaccharide is not particularly limited and may be any of sheet, powder, fiber and granular forms.

The alcohol compound is not particularly limited as long as it is free of an acetal structure. Aliphatic alcohols of 1 to 10 carbon atoms are preferred. The alcohol compound should be of 1 to 10 carbon atoms, preferably 1 to 5 carbon atoms, more preferably 1 to 3 carbon atoms from the aspect of using an alcohol compound of small structure which can penetrate into interstices in the molecular structure of the polysaccharide to act on the reducing end-group within the bulk thereof.

Suitable aliphatic alcohols include monohydric aliphatic alcohols such as methanol, ethanol, propanol, isopropanol, n-butanol, and cyclohexanol; alkylene glycol monoalkyl ethers such as ethylene glycol monomethyl ether (or 2-methoxyethanol) and diethylene glycol monomethyl ether (or 2-(2-methoxyethoxy)ethanol); alkylene glycols such as ethylene glycol and propylene glycol; and polyhydric aliphatic alcohols, e.g., glycerin and sugar alcohols such as erythritol, xylitol, mannitol, and glucitol.

From the aspect of using an alcohol compound of small structure which can penetrate into interstices in the molecular structure of the polysaccharide to act on the reducing end-group within the bulk thereof, monohydric aliphatic alcohols of 1 to 3 carbon atoms, alkylene glycols of 2 or 3 carbon atoms, and glycerin are preferred, with methanol, ethylene glycol and glycerin being especially preferred. The alcohol compound may be used alone or in admixture of two or more.

The method of adding the alcohol compound is not particularly limited as long as the polysaccharide having a reducing end-group and the alcohol compound can be kept mixed prior to heating in the first heating step. There may be used either a method of adding the alcohol compound to the polysaccharide having a reducing end-group or a method of adding the polysaccharide having a reducing end-group to the alcohol compound. The alcohol compound may be either liquid or gas. For example, it is recommended to add a liquid alcohol compound to a porous cellulose sheet (i.e., filter) so that the cellulose sheet is impregnated with the alcohol compound.

The amount of the alcohol compound added may be a sufficient amount to undergo dehydrating condensation reaction with the reducing end-group of the polysaccharide to form a glycosidic bond, preferably at least 10 parts by weight, more preferably at least 30 parts by weight per 100 parts by weight of the polysaccharide having a reducing end-group. The upper limit of the amount of the alcohol compound added is not critical. If the amount of the alcohol compound added is less than 10 parts by weight, there is a risk that the formation of a glycosidic bond between the reducing end-group of the polysaccharide and the alcohol compound is insufficient. When an alcohol compound-containing gas is blown into the polysaccharide, the concentration of the alcohol compound in the gas is preferably 0.05 to 0.45 mol/L.

The heating temperature in the first heating step is in a range of 130 to 350° C., preferably 150 to 320° C., more preferably 170 to 300° C., from the aspect of reacting the reducing end-group of the polysaccharide with the alcohol compound to form a glycosidic bond. If the heating temperature is lower than 130° C., the glycosidic bond of the reducing end-group of the polysaccharide with the alcohol compound is not fully formed. If the heating temperature exceeds 350° C., the pyrolysis of the polysaccharide (typically cellulose) starts. Although the heating temperature used herein is the internal temperature of the heating unit for heating the polysaccharide and alcohol compound, it may be regarded as the temperature of the polysaccharide itself (i.e., bulk temperature).

The heating unit is not particularly limited as long as the object can be heated at the desired temperature. For example, a muffle furnace, electric furnace, infrared furnace, microwave-assisted synthesizer or the like may be used.

The heating time of the first heating step is preferably 5 to 90 minutes, more preferably 10 to 60 minutes from the aspect of reacting the reducing end-group of the polysaccharide with the alcohol compound to form a glycosidic bond.

The first heating step may be followed by washing with deionized water and drying, if necessary, from the aspect of removing the unreacted alcohol compound.

[Step (2): Second Heating Step]

The second heating step is to conduct second heat treatment of heating the first heat treated polysaccharide for pyrolysis to form a gaseous sugar anhydride, the second heat treatment forming no char or only filmy char and forming no carbon monoxide or some carbon monoxide such that the amount of carbon monoxide formed is not more than 5 parts by weight per 100 parts by weight of the absolute dry weight of the polysaccharide.

In the second heat treatment, preferably the temperature of the polysaccharide itself (i.e., bulk temperature) reaches 400 to 500° C.

In the second heat treatment, the temperature at which the polysaccharide is heated (i.e., bulk temperature) can be estimated from whether or not char (i.e., carbonized solid residue) is formed, the state of char if formed, and the composition of gas (specifically, whether or not carbon monoxide is formed, and the amount of carbon monoxide if formed). When the bulk temperature of the polysaccharide is lower than 400° C., the char maintains the shape of the original polysaccharide. When the bulk temperature of the polysaccharide is equal to or higher than 400° C., no char is formed, or if char is formed, the char is liquefied at the heating temperature and then becomes filmy char. See J. Anal. Appl. Pyrolysis 109 (2014) pp. 185-195. When the bulk temperature of the polysaccharide exceeds 500° C., the sugar anhydride resulting from pyrolysis undergoes further fragmentation to form mainly carbon monoxide. See ChemSusChem, 8 (2015) pp. 2240-2249. The amount of carbon monoxide formed at this point exceeds 5 parts by weight per 100 parts by weight of the absolute dry weight of the polysaccharide.

Accordingly, when the first heat treated polysaccharide is heat treated, and the second heat treatment forms no char or only filmy char and forms no carbon monoxide or some carbon monoxide such that the amount of carbon monoxide formed is not more than 5 parts by weight per 100 parts by weight of the absolute dry weight of the polysaccharide, it is estimated that the bulk temperature of the polysaccharide is in the range of 400 to 500° C. The amount of carbon monoxide formed is preferably up to 3 parts by weight, more preferably up to 1 part by weight, even more preferably up to 0.5 part by weight, per 100 parts by weight of the absolute dry weight of the polysaccharide. The lower limit of the amount of carbon monoxide formed is 0 part by weight.

When it is estimated that the bulk temperature of the polysaccharide after heating is lower than 400° C., the heating is insufficient, with the risk that part of the polysaccharide is not pyrolyzed, the pyrolysis reaction lowers its selectivity to form more by-products, or the sugar anhydride formed liquefies and polymerizes. When it is estimated that the bulk temperature of the polysaccharide after heating exceeds 500° C., there is a possibility that the sugar anhydride resulting from pyrolysis undergoes fragmentation, that is, it is decomposed into smaller molecules such as carbon monoxide, carbon dioxide, methane and ethylene. It is noted that the temperature of the polysaccharide can also be measured directly by any well-known means such as thermocouple and IR radiation thermometer.

The heating rate of the second heating step is preferably at least 10° C./sec, more preferably at least 30° C./sec, even more preferably at least 50° C./sec from the aspect of preventing the risk that the pyrolysis reaction of polysaccharide lowers its selectivity to form more by-products, or the sugar anhydride formed liquefies and polymerizes. The upper limit of the heating rate is not critical, but is up to 5,000° C./sec from the aspect of handling.

The heating time of the second heating step (that is, heating time from the point of time when the bulk temperature of the polysaccharide has reached the estimate temperature of 400 to 500° C.) is preferably 60 seconds at the longest, more preferably up to 30 seconds, even more preferably up to 15 seconds, most more preferably up to 10 seconds, from the aspect of production efficiency of the target product and the aspect of suppressing a loss of yield caused by secondary decomposition by reactions in low-temperature and over-heat regions.

The heating method in the second heating step is not particularly limited. Examples include a method of indirect heating by irradiation of IR radiation or micro-wave, a method of heating by contact with hot gas, e.g., air or nitrogen in a fluidized bed or the like, a method of heating by direct contact with a hot jacket wall or impeller in a mixing tank or the like, and a combination thereof. The method of indirect heating by irradiation of IR radiation is preferred for the reason that since the surrounding atmosphere is not heated, and hence, the gaseous sugar anhydride formed can be quenched, and secondary decomposition of the sugar anhydride is inhibited.

The heating step may be either a batch process involving feeding a given amount of the raw material, polysaccharide to the heating unit, heat treating it and recovering the product, or a continuous process involving continuously feeding the raw material, polysaccharide to the heating unit and continuously recovering the product.

Further, the atmosphere of the heating unit for conducting heat treatment is not limited to atmospheric pressure. From the aspect of optimum process design, an inert gas atmosphere may be adopted under reduced pressure or applied pressure.

The sugar anhydride resulting from the second heating step is typically gaseous and specifically, levoglucosan when cellulose or starch is used as the polysaccharide, and xylosan, levoglucosan, mannosan, galactosan or a mixture thereof when hemicellulose is used.

7

8

[Step (3): Recovery Step]

The recovery step is the step of cooling the gaseous sugar anhydride resulting from the second heating step to a temperature not higher than the boiling point thereof and recovering the sugar anhydride. Since the sugar anhydride formed undergoes secondary decomposition at or below about 400° C., it is quenched to or below 100° C. at which it remains stable, for preventing the sugar anhydride from secondary decomposition and increasing the yield of the target, sugar anhydride.

The recovery method is not particularly limited when the gaseous sugar anhydride can be cooled to a temperature equal to or lower than its boiling point. Exemplary are a method of rapidly mixing the hot gas stream containing the gaseous sugar anhydride with cold air or nitrogen to cool it into an aerosol form for recovery, a method of bringing the gaseous sugar anhydride in contact with cold liquid in a scrubber or the like and dissolving therein for recovery, and a method of bringing the gaseous sugar anhydride in contact with a cold solid to convert it to a liquid or solid form for recovery.

When the sugar anhydride is levoglucosan, for example, it is preferably cooled at or below 300° C., more preferably at or below 200° C., even more preferably at or below 100° C.

<Method for Producing Saccharide>

The invention also provides a method for producing a saccharide comprising the step of hydrolyzing the sugar anhydride obtained by the aforementioned method in the presence of a solid acid catalyst while heating.

While the solid acid catalyst is not particularly limited, examples thereof include cation exchange resins such as polystyrene sulfonic acid, inorganic oxides such as silica-alumina and zeolite, and polyphosphoric acid. The catalysts may be used alone or in admixture of two or more.

Although the amount of the solid acid catalyst used is not particularly limited, the amount is preferably 100 to 5,000,000 parts by weight, more preferably 200 to 10,000 parts by weight, even more preferably 300 to 1,000 parts by weight per 100 parts by weight of the sugar anhydride, from the aspect of smooth progress of reaction.

While the method of performing hydrolysis is not particularly limited, a method of mixing a solution of the sugar anhydride with the solid acid catalyst by stirring, and a method of passing a solution of the sugar anhydride through a column packed with the solid acid catalyst are exemplary.

Examples of the solvent for preparing the solution of the sugar anhydride include water, tetrahydrofuran (THF), N,N-dimethylformamide (DMF), acetone, and acetonitrile, with water being preferred from the economy aspect. The solvent may consist of water or a mixture of water and an organic solvent as mentioned above. The amount of water in the solvent is preferably at least 500 moles per 100 moles of the sugar anhydride from the aspect of smooth progress of reaction.

While the concentration of sugar anhydride in the sugar anhydride solution is not particularly limited, the concentration is preferably 0.001 to 50% by weight, more preferably 0.1 to 30% by weight, even more preferably 1 to 30% by weight, from the aspect of obtaining a high concentration sugar solution.

The heating unit is not particularly limited as long as the object can be heated at the desired temperature. For example, a muffle furnace, electric furnace, infrared furnace, microwave-assisted synthesizer or the like may be used. The microwave-assisted synthesizer is preferred from the aspect of selectively heating the solid acid to forward the reaction efficiently. The heating temperature is preferably 80 to 200° C., more preferably 90 to 180° C., even more preferably 100 to 160° C. from the aspect of obtaining the saccharide in high yields. While the heating may be continued until the sugar anhydride is consumed, the heating time is preferably 1 to 120 minutes, more preferably 3 to 60 minutes, even more preferably 5 to 30 minutes from the aspect of suppressing side reactions.

It is noted that even when a sugar anhydride obtained by a method other than the aforementioned method is used, a saccharide is similarly obtained from hydrolysis in the presence of a solid acid catalyst.

The saccharide resulting from hydrolysis is glucose from levoglucosan which is used as the sugar anhydride, xylose from xylosan, mannose from mannosan, or galactose from galactosan.

EXAMPLES

Examples and Comparative Examples are given below for illustrating the invention although the invention is by no means limited by Examples. The quantitative analyses used in Examples are shown below.

Quantitative Analysis of Levoglucosan in Example 1 and Comparative Examples 1, 2

The amount of levoglucosan in Example 1 and Comparative Examples 1, 2 was determined by $^1$H-NMR under the following conditions.

Sample solvent: 0.7 mL deuterated dimethyl sulfoxide having added thereto 5 mg of oxime reagent (NH$_2$OH—HCl) and one droplet of heavy water Internal standard: 0.46 mg maleic acid System: nuclear magnetic resonance system, Bruker Avance III 400

[Quantitative Analysis of Carbon Monoxide, Methane and Hydrogen]

The amount of the gas (carbon monoxide, methane and hydrogen) resulting from the second heating step was determined by gas chromatography under the following conditions.

System: CP-4900 Micro GC by Varian Inc.

Column: CP-Molsieve 5 Å (length 10 m, ID 0.32 mm, film thickness 0.12 μm, by Agilent Technologies)

Detector: thermal conductivity detector (μTCD)

Carrier gas: 15 mL/min of argon

Column temperature: 100° C.

[Quantitative Analysis of Carbon Dioxide and Ethylene]

The amount of the gas (carbon dioxide and ethylene) resulting from the second heating step was determined by gas chromatography under the following conditions.

System: CP-4900 Micro GC by Varian Inc.

Column: CP-PoraPLOT Q (length 10 m, ID 0.32 mm, film thickness 0.10 μm, by Agilent Technologies)

Detector: thermal conductivity detector (μTCD)

Carrier gas: 15 mL/min of helium

Column temperature: 80° C.

The sum of amounts of carbon monoxide, methane, hydrogen, carbon dioxide, and ethylene is the total amount of the gas.

Quantitative Analysis of Glucose and Levoglucosan in Example 2

The amount of glucose and levoglucosan in Example 2 was determined by ion chromatography under the following conditions.

Sample solvent: deionized water

System: ion chromatograph LC-20 ADsp by Shimadzu Corp.

Detector: electrochemical detector DECADE Elite SCC 175.0035 by Antec Scientific Guard column: Dionex CarboPac™ PA1 by Thermo Scientific (particle size 10 μm, ID 4 mm, length 50 mm)

Column: Dionex CarboPac™ PA1 by Thermo Scientific (particle size 10 μm, ID 4 mm, length 250 mm)

Mobile phase: mixture of 85 vol % of deionized water and 15 vol % of 0.2 mol/L sodium hydroxide aqueous solution, flow rate 1 mL/min Injection volume: 10 μL Column temperature: 35° C.

Example 1

Cellulose (Whatman No. 42 filter, length 4.3 cm, width 1.0 cm, thickness 0.2 mm, weight 30 mg) was placed into a test tube charged with 13 g of glycerin, and heated in a maffle furnace of nitrogen atmosphere at 280° C. for 30 minutes (first heating step). By washing with deionized water, drying in an oven at 105° C. overnight, and resuming room temperature (20° C.) for air drying, the cellulose having undergone the first heating step was obtained.

Next, using an IR furnace (Infrared Gold Image Furnace RHL-E45N by Advance Riko, Inc., lamp voltage 100 V, power 4.0 kW, heating length 140 mm, tube inner diameter 52 mm), the cellulose resulting from the first heating step was heated while flowing nitrogen through the reaction tube of the IR furnace (second heating step). The IR furnace was set to an output power of 2.0 kW, a heating time of 10 inner wall of the gas bag was recovered by dissolving in 200 mL of methanol. Using an evaporator to remove methanol from a 60-mL portion of the recovered methanol solution, a solvent-extracted component was obtained.

The solvent-extracted component was dissolved in 0.7 mL of deuterated dimethyl sulfoxide. By $^1$H-NMR spectroscopy, it was identified to be levoglucosan. The yield was determined to be 78.2 parts by weight of levoglucosan per 100 parts by weight of the absolute dry weight of cellulose.

Comparative Example 1

Levoglucosan was obtained by the same procedure as in Example 1 except that the first heating step was omitted. The yield of levoglucosan was 52.7 parts by weight per 100 parts by weight of the absolute dry weight of cellulose. Also, filmy char formed in the IR furnace at the end of the heating step.

Comparative Example 2

Levoglucosan was obtained by the same procedure as in Example 1 except that the first heating step was omitted and the IR furnace in the second heating step was set to an output power of 4.0 kW. The yield of levoglucosan was 42.6 parts by weight per 100 parts by weight of the absolute dry weight of cellulose. Also, filmy char formed in the IR furnace at the end of the heating step.

The results of Example 1 and Comparative Examples 1, 2 are tabulated in Table 1.

TABLE 1

| | Concentration of levoglucosan in solvent-extracted component (wt %) | Yield (based on absolute dry weight of cellulose) | | | | | |
|---|---|---|---|---|---|---|---|
| | | Solvent-extracted component | | | | Gas | |
| | | Total amount (wt %) | Levoglucosan (wt %) | Glycol aldehyde (wt %) | Char (wt %) | Total amount (wt %) | Carbon monoxide (wt %) |
| Example 1 | 84.0 | 93.1 | 78.2 | 1.6 | 4.1 | 2.8 | 0 |
| Comparative Example 1 | 55.9 | 94.3 | 52.7 | 4.6 | 1.2 | 4.5 | 0 |
| Comparative Example 2 | 50.8 | 83.8 | 42.6 | 4.8 | 4.1 | 12.1 | 5.32 | seconds, and a linear speed of nitrogen of 2.4 m/min. The reaction tube of the IR furnace was equipped at its outlet with a gas-sampling bag (Tedlar bag, volume 5 L) containing 30 mL of methanol.

It is estimated that since filmy char formed in the IR furnace at the end of the second heating step, and no carbon monoxide was detected, the second heating step was conducted at 400 to 500° C. It is also estimated that since filmy char formed in a heating time of 10 seconds, the heating rate was at least 70° C./sec.

The gaseous product resulting from heating was cooled with nitrogen flow into an aerosol form, which was collected in the gas bag (recovery step). After the gas bag was kept stationary for 30 minutes, 5 mL of neon gas as reference material was fed into the gas bag. The gas was identified and quantified by gas chromatography.

Thereafter, the methanol having the product dissolved therein was recovered, and the product agglomerated on the It is evident from the results of Example 1 and Comparative Example 1 that by conducting the first heating step prior to the second heating step, the sugar anhydride (levoglucosan) was obtained from the polysaccharide (cellulose) in high yields and with a high purity (concentration of levoglucosan in solvent-extracted component). Since the polysaccharide whose reducing end-group had been protected with a group derived from the alcohol compound through the first heating step was used in Example 1, formation of gas and glycol aldehyde from pyrolysis of the polysaccharide at about 350° C. was suppressed. It is thus estimated that pyrolysis took place mostly at 400 to 500° C. in the second heating to step. As a result, levoglucosan was selectively formed.

Example 2

By removing methanol from 2 mL of the methanol solution recovered in Example 1 on an evaporator, the solvent-extracted component in Example 1 was obtained. Then, the solvent-extracted component was transferred to a reactor of 10 mL volume. 4 mL of distilled water was added to a solid acid catalyst (Amberlyst 15 JWET, bulk volume 2 mL) immersed in distilled water, followed by thorough shaking/mixing. Thereafter, 1 mL of the supernatant was taken out and analyzed by ion chromatography, finding that the concentration of levoglucosan solution was 0.0076% by weight.

With stirring by a stirrer, the solution was heat treated at 120° C. for 30 minutes by microwave heating. For the microwave heating, a microwave synthesizer (Discover SP by CEM Corporation) was used.

After the heat treatment, the yield of glucose was determined by ion chromatography.

As a result, there was obtained 94 parts by weight of glucose per 100 parts by weight of the absolute dry weight of cellulose, or 126 parts by weight of glucose per 100 parts by weight of levoglucosan. That is, 113 moles of glucose was obtained from 100 moles of levoglucosan in Example 2.

It is noted that the amount of glucose exceeded the amount of levoglucosan for the reason that oligosaccharides such as cellobiosan in the solvent-extracted component in Example 1 were hydrolyzed to form glucose.

Reference Example 1

A 0.02 wt % levoglucosan reference solution was prepared by dissolving 10 mg of levoglucosan (manufactured by Tokyo Chemical Industry Co., Ltd., purity >99.0%) in 50 mL of distilled water. Thereafter, 30 mL of distilled water was added to a solid acid catalyst (Amberlyst 15 JWET, bulk volume 20 mL) immersed in distilled water and further, 10 mL of the levoglucosan reference solution was added, followed by thorough shaking/mixing. 1 mL of the supernatant was taken out and analyzed by ion chromatography, finding that the concentration of levoglucosan solution was 0.0048% by weight. Thereafter, the solid acid catalyst (bulk volume 2 mL) and the supernatant (3 mL) were taken out and fed to a reactor of 10 mL volume. With stirring by a stirrer, the solution was heat treated at 120° C. for 22.5 minutes by microwave heating on a microwave synthesizer.

After the heat treatment, the yield of glucose was determined by ion chromatography, finding that 93.7 parts by weight of glucose was obtained per 100 parts by weight of levoglucosan.

Reference Example 2

The same procedure as in Reference Example 1 was carried out except that the heat treatment conditions were changed to 140° C. and 7.5 minutes.

Reference Example 3

The same procedure as in Reference Example 1 was carried out except that the concentration of levoglucosan solution was 10% by weight and the heat treatment conditions were changed to 140° C. and 7.5 minutes.

The results of Example 2 and Reference Examples 1 to 3 are tabulated in Table 2.

TABLE 2

| | Concentration of levoglucosan solution (wt %) | Heating temperature (° C.) | Heating time (min) | Yield of glucose based on levoglucosan weight (wt %) |
|---|---|---|---|---|
| Example 2 | 0.0076 | 120 | 30 | 126.0 |
| Reference Example 1 | 0.0048 | 120 | 22.5 | 93.7 |
| Reference Example 2 | 0.0048 | 140 | 7.5 | 93.3 |
| Reference Example 3 | 10 | 140 | 7.5 | 91.0 |

It is evident from the results of Example 2 and Reference Examples 1 to 3 that the sugar anhydride could be converted to saccharide by the simple step of heating in the presence of a solid acid catalyst. The solvent-extracted component containing the sugar anhydride obtained from the inventive method contains by-produced oligosaccharides. Then, when the solvent-extracted component is heated in the presence of a solid acid catalyst, the oligosaccharide is also converted to saccharide through hydrolysis so that the yield of saccharide is increased. The saccharide solution and the solid acid catalyst are readily separated by filtration or the like. Further, it is found possible to concentrate the saccharide solution to a high concentration which is required for the saccharide solution to be used as fermentation raw material.

The invention claimed is:

1. A method for producing a sugar anhydride, comprising:
   (1) a first heat treatment step of heating a raw material, polysaccharide having a reducing end-group at a temperature of from 280° C. to 350° C. in the presence of an alcohol compound of 1 to 10 carbon atoms free of an acetal structure,
   (2) a second heat treatment step of heating the first heat treated polysaccharide for pyrolysis to form a gaseous sugar anhydride, the second heat treatment forming no char or only filmy char and forming no carbon monoxide or some carbon monoxide such that the amount of carbon monoxide formed is not more than 5 parts by weight per 100 parts by weight of the absolute dry weight of the second heat treated polysaccharide, and
   (3) a recovery step of cooling the gaseous sugar anhydride to a temperature not higher than the boiling point thereof and recovering the sugar anhydride.

2. The method of claim 1 wherein the second heat treatment step includes irradiating infrared radiation for heating.

3. The method of claim 1 wherein in the second heat treatment step, the first heat treated polysaccharide is heated for 60 seconds at the longest.

4. The method of claim 1 wherein in the second heat treatment step, the bulk temperature of the second heat treated polysaccharide itself is 400 to 500° C.

5. The method of claim 1 wherein the alcohol compound of 1 to 10 carbon atoms free of an acetal structure is at least one compound selected from monohydric aliphatic alcohols of 1 to 3 carbon atoms, alkylene glycols of 2 or 3 carbon atoms, and glycerin.

6. The method of claim 1 wherein the raw material, polysaccharide having the reducing end-group is cellulose.

7. The method of claim 1 wherein the sugar anhydride is levoglucosan.

8. The method of claim 1 wherein the raw material, polysaccharide is in sheet, powder, fiber, or particle form.

9. The method of claim 1 wherein the raw material, polysaccharide is a raw material consisting essentially of polysaccharide having a reducing end-group.

* * * * *